United States Patent
Rudo

(10) Patent No.: US 9,138,298 B2
(45) Date of Patent: Sep. 22, 2015

(54) FIBER REINFORCED DENTAL APPLIANCES AND PROSTHESES

(75) Inventor: David Rudo, Seattle, WA (US)

(73) Assignee: Ribbond, Inc., Seattle, WA (US)

( * ) Notice: Subject to any disclaimer, the term of this patent is extended or adjusted under 35 U.S.C. 154(b) by 224 days.

(21) Appl. No.: 13/544,712

(22) Filed: Jul. 9, 2012

(65) Prior Publication Data

US 2013/0017510 A1    Jan. 17, 2013

Related U.S. Application Data

(60) Provisional application No. 61/507,081, filed on Jul. 12, 2011.

(51) Int. Cl.
| | |
|---|---|
| *A61C 8/00* | (2006.01) |
| *A61C 5/00* | (2006.01) |
| *D03D 3/00* | (2006.01) |
| *D03D 15/00* | (2006.01) |
| *D03D 19/00* | (2006.01) |
| *D03D 1/00* | (2006.01) |

(52) U.S. Cl.
CPC ........ *A61C 5/007* (2013.01); *D03D 1/00* (2013.01); *D03D 3/005* (2013.01); *D03D 15/0094* (2013.01); *D03D 19/00* (2013.01); *D10B 2505/02* (2013.01); *D10B 2509/00* (2013.01); *Y10T 442/102* (2015.04); *Y10T 442/30* (2015.04)

(58) Field of Classification Search
CPC ...... A61C 8/0048; A61C 8/005; D03D 19/00; D03D 15/00
USPC .................................. 433/172–176, 215, 229
See application file for complete search history.

(56) References Cited

U.S. PATENT DOCUMENTS

| | | | |
|---|---|---|---|
| 2,810,405 A | * | 10/1957 | Huau ........................ 139/383 R |
| 3,957,067 A | | 5/1976 | Ferraro et al. |
| 4,321,042 A | | 3/1982 | Scheicher |
| 4,381,918 A | | 5/1983 | Ehrnford |
| 4,410,586 A | | 10/1983 | Ladizesky et al. |
| 4,665,951 A | | 5/1987 | Ellis |
| 4,717,341 A | | 1/1988 | Goldberg et al. |

(Continued)

FOREIGN PATENT DOCUMENTS

| | | |
|---|---|---|
| EP | 0221223 A2 | 5/1987 |
| EP | 1704827 A1 | 9/2006 |

(Continued)

OTHER PUBLICATIONS

International Search Report and Written Opinion mailed Dec. 4, 2012 in Application No. PCT/US2012/046548 filed Jul. 12, 2012.

(Continued)

*Primary Examiner* — Yogesh Patel

(74) *Attorney, Agent, or Firm* — Kilpatrick Townsend & Stockton, LLP

(57) ABSTRACT

A fabric ribbon for use in dental applications. The fabric ribbon includes a transverse set of fibers aligned generally transverse to a length of the ribbon; and a axial set of fibers, intertwined around the transverse set of fibers and aligned generally axially along the length of the ribbon, each of the axial set of fibers having a thickness greater than a thickness of each of the transverse set of fibers. The fabric ribbon may be used for a dental appliance, for example in a periodontal splint, a pontic beam, a composite restoration, or to bridge a crack in teeth.

12 Claims, 2 Drawing Sheets

(56) References Cited

U.S. PATENT DOCUMENTS

| | | |
|---|---|---|
| 4,731,020 A | 3/1988 | Kawahara et al. |
| 4,738,622 A | 4/1988 | Kawahara et al. |
| 4,816,028 A | 3/1989 | Kapadia et al. |
| 4,836,226 A | 6/1989 | Wolak |
| 4,944,987 A | 7/1990 | Cordia et al. |
| 4,960,349 A | 10/1990 | Willibey et al. |
| 5,176,951 A * | 1/1993 | Rudo .......................... 442/220 |
| 5,752,550 A * | 5/1998 | Scari' et al. ............... 139/420 C |
| 5,786,283 A | 7/1998 | Borer |
| 5,843,542 A * | 12/1998 | Brushafer et al. ........... 428/36.1 |
| 7,186,760 B2 | 3/2007 | Rudo |
| 7,673,550 B2 | 3/2010 | Karmaker et al. |
| 2006/0204712 A1 | 9/2006 | Gardner et al. |
| 2007/0037462 A1 | 2/2007 | Allen et al. |

FOREIGN PATENT DOCUMENTS

| | | |
|---|---|---|
| FR | 2561789 A1 | 9/1985 |
| JP | 2185453 A | 7/1990 |
| JP | 2003020542 A | 1/2003 |

OTHER PUBLICATIONS

JP2014-520340, "Office action" mailed Jan. 21, 2015, 6 pages.

* cited by examiner

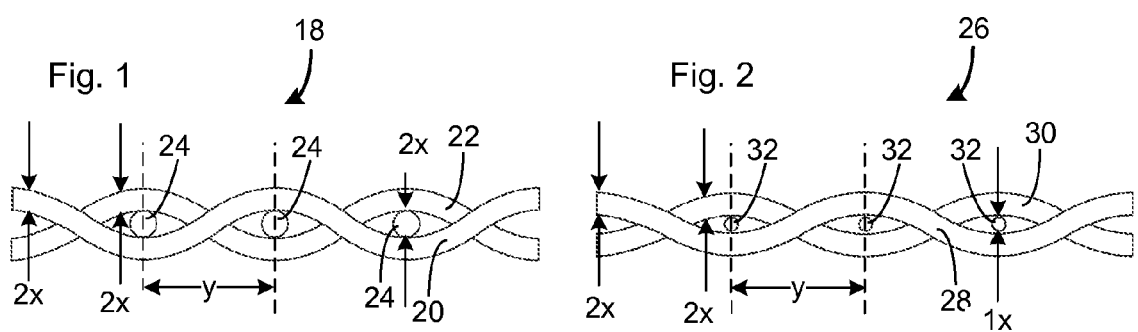
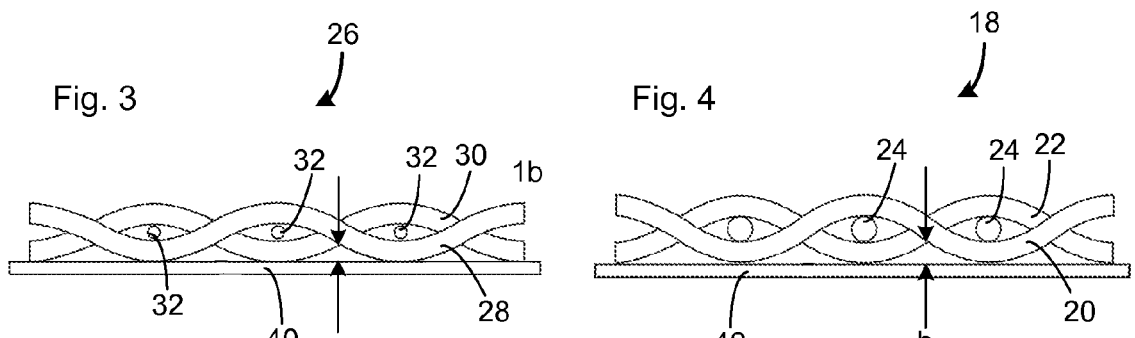

FIBER REINFORCED DENTAL APPLIANCES AND PROSTHESES

CROSS-REFERENCES TO RELATED APPLICATIONS

This application claims the benefit of U.S. Provisional Application No. 61/507,081, filed on Jul. 12, 2011, the full disclosure of which is incorporated herein by reference.

BACKGROUND

Reinforced plastics are combinations of fibers and polymeric binders, typically resins. The combination of the fibers and the binder form a composite material that can achieve a balance of material properties that are superior to the properties of either the fibers or the binder.

The combination of strong fibers and synthetic polymer binders to form reinforced plastics derives from several basic considerations of material science: the inherent strength of fine fibers, the wetting requirement for adhesion between the fibers and the binder, and the ease of the liquid-solid phase change of synthetic polymer binder. In a general sense, the polymeric binder matrix serves the purpose of a supporting medium surrounding each fiber and separating it from its neighbors, and stabilizing it against bending and buckling. These functions are best fulfilled when there is good adhesion between the fibers and the binder matrix. Adhesion can be fostered by utilizing a relatively low-viscosity liquid polymeric precursor to impregnate a reinforcing fiber material, followed by polymerization of the binder matrix. Adhesion can also be enhanced by plasma surface treatment of the fibers.

Two broad categories of polymeric materials have been typically utilized for the binder when preparing reinforced plastics. These two types are thermoplastic polymers, which generally melt in the range of 150° C. to 250° C. and readily solidify upon cooling, and thermosetting polymers which pass through a liquid phase just once during their life, while they are being polymerized and cross-linked into heat-infusible forms.

The two predominant types of fibers that have been used in reinforced plastics, considering all uses of composites, have been glass and cellulose fibers. Fibrous glass comprises well over 90% of the fibers used in reinforced plastics because it is inexpensive to produce and possesses high-strength, high-stiffness, low specific gravity, chemical resistance, and good insulating characteristics. In reinforced plastics, glass has been used in various forms. Fibrous glass can been chopped into short lengths (6-76 mm) and gathered into a felt or matte, resulting in a form that is easy to handle and low in cost. Previously, it has been observed that advantageous strength properties can be achieved in the final composite with non-woven fabrics in which all the fibers are straight, continuous, and aligned parallel in a single direction.

In addition to glass and cellulose fibers, other types of fibers have also been used to reinforce plastic materials. The stiffest fibers known are composed of graphite, which theoretically can be almost five times more rigid than steel. However, despite much work over many years by many technical organizations, the cost of graphite fibers remains high. As a result, their use in composites is limited to applications that place a premium on weight savings: aircraft, missiles, sports equipment, etc.

In 1971, aromatic polyamide fibers became widely commercially available and are presently being used extensively in automotive tires and numerous aerospace structures. The aromatic polyamides are designated as "aramids" by the Federal Trade Commission, and that is the term used herein to refer to them. One specific aramid that has been widely used in many applications is referred to as KEVLAR. Discovered in 1965, KEVLAR is produced and marketed by DuPont.

In the stiffness range between glass and steel, aramids are lighter than glass, comparatively strong, much tougher, and absorb considerable energy before breaking, even under impact conditions. The fibers are highly crystalline and directional in character. KEVLAR fibers are known to have excellent resistance to flame and heat, organic solvents, fuels and lubricants, and they can be woven into fabric. Because of their strength and other properties, aramid fibers have been used in sports equipment, and in protective systems where ballistic stopping exploits their superior impact resistance.

Fibers of ultra-high strength polyethylene have been produced. Such fibers are available from Honeywell Advanced Fibers and Composites, Colonial Heights, Va., under the trademark SPECTRA, and Dutch State Mining Corporation ("DSM"). The fibers are made of extended chain polyethylene and have a low specific gravity of about 0.97, which is less than the specific gravity of fiberglass or aramid fibers.

Reinforced plastics are also used in medical and dental applications. As an example, U.S. Pat. No. 5,176,951, owned by the present applicant, discloses a method of reinforcing a dental appliance or prosthesis utilizing a reinforced plastic. The method disclosed therein includes the acts of applying to a resin portion of the dental appliance or prosthesis a lightweight, woven aramid or extended chain polyethylene fabric, and covering the fabric with more of the resin. Also disclosed are reinforcing materials (preferably a plasma-coated SPECTRA fabric), and dental appliances or prostheses reinforced by a lightweight, woven aramid or extended chain polyethylene fabric. While the methods and materials disclosed therein work well for their intended purposes, the methods and materials herein provide improvements.

DESCRIPTION OF THE BACKGROUND ART

The following references may describe relevant background art:
U.S. Pat. No. 3,957,067
U.S. Pat. No. 4,321,042
U.S. Pat. No. 4,381,918
U.S. Pat. No. 4,410,586
U.S. Pat. No. 4,665,951
U.S. Pat. No. 4,717,341
U.S. Pat. No. 4,731,020
U.S. Pat. No. 4,738,622
U.S. Pat. No. 4,816,028
U.S. Pat. No. 4,836,226
U.S. Pat. No. 4,960,349
U.S. Pat. No. 4,944,987
U.S. Pat. No. 7,186,760
U.S. Pat. No. 7,673,550
European Patent Application No. 0,221,223

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with embodiments, a fabric ribbon is provided for use in a reinforced plastic composite. The fabric ribbon includes a transverse set of fibers aligned generally transverse to a length of the ribbon; and an axial set of fibers, intertwined around the transverse set of fibers and aligned generally axially along the length of the ribbon, each of the axial set of fibers having a thickness greater than a thickness of each of the transverse set of fibers.

In embodiments, the fabric ribbon is a leno weave fabric. The transverse set of fibers may be weft fibers for the leno weave fabric and the axial set of fibers may be warp fibers for the leno weave fabric.

In specific embodiments, a ratio of the diameter of the axial set of fibers to the transverse set of fibers is at least 1.1 to 1, greater than or equal to 2 to 1, or greater than or equal to 6 to 1.

In embodiments, the fabric ribbon is used as a dental appliance.

Additional embodiments herein are directed to a method of reinforcing a tooth or teeth of a patient. The method includes applying a fabric ribbon to a patient's tooth or teeth. The fabric ribbon includes a transverse set of fibers aligned generally transverse to the length of the ribbon; and an axial set of fibers, intertwined around the transverse set of fibers and aligned generally axially along the length of the ribbon, each of the axial set of fibers having a thickness greater than the thickness of each of the transverse set of fibers. The fabric ribbon is bonded to the patient's tooth or teeth using a resin.

In embodiments of the method, applying the fabric ribbon includes applying the fabric ribbon over multiple teeth so as to form a periodontal splint, applying the fabric ribbon comprises applying the fabric ribbon over multiple teeth so as to form a pontic beam, applying the fabric ribbon on a single tooth so as to form a composite restoration, and/or applying the fabric ribbon across a crack in a single tooth to bridge the crack.

For a fuller understanding of the nature and advantages of the present invention, reference should be made to the ensuing detailed description and accompanying drawings.

BRIEF DESCRIPTION OF THE DRAWINGS

FIG. 1 is cross section of a prior art fabric ribbon used in dental applications;

FIG. 2 is a cross section of a fabric ribbon in accordance with embodiments herein;

FIG. 3 is a cross section of the fabric ribbon of FIG. 2 shown applied to a substrate;

FIG. 4 is a cross section of the fabric ribbon of FIG. 1 shown applied to a substrate;

DETAILED DESCRIPTION

Figure 5:
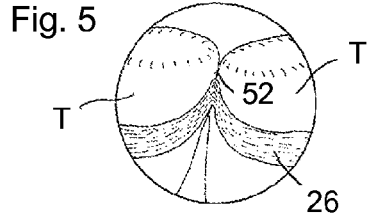
FIGS. 5 and 6 are representations of applications of the fabric ribbon of FIG. 2 to form a periodontal splint.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments herein are directed to reinforced plastics, and more specifically, resin impregnated composites, for use in dental applications, including, but not limited to, crowns, bridges, frameworks, clasps, inlays, onlays, fillings, splints, partial and full dentures, implants, posts, cores and other orthodontic applications. The dental appliances or prostheses described herein are improvement of the reinforced dental appliances and prostheses described in U.S. Pat. No. 5,176,951, incorporated herein by reference. That patent is directed to, inter alia, the use of leno weave fabrics with a resin to form a dental fiber composite. A leno weave fabric, also called a "gauze weave," is a weave structure in which paired warp yarns are intertwined in a series of figure eights and filling yarn (weft yarn) is passed through each of the interstices so formed, producing a firm, open mesh. In other words, the weave includes warp yarns that are twisted together in pairs around and on weft or filling yarns of the mesh.

In the '951 patent, ribbons are formed from leno weave, with the axially aligned fibers that extend the length of the fabric being the intertwined figure eight yarns, and the transverse fibers extending transverse to the ribbon. The ribbons are used in dental applications. For the fabric ribbon in the '951 patent, the warp yarns (axially aligned yarns), and the weft or transverse fibers (transversely aligned yarns) are of the same thickness and deniers. In contrast, in accordance with embodiments herein, the axial and transverse yarns of are of different thickness or denier. Specifically, the axial yarns are of greater thickness than the transverse yarns.

Although embodiments described herein utilize a leno weave, other fabric weaves may be used, such as a plain weave, a triaxial braided fabric, or other weave structures. In general, however, in accordance with embodiments herein, reinforced plastic ribbons are utilized in dental appliances, and the fibers in the reinforced plastics are formed in a weave in which the axial yarns (i.e., yarns generally extending along the length of the ribbon) are of greater thickness than transverse yarns (i.e., yarns extending generally perpendicular or at an angle to the length of the ribbon).

Thicknesses of the axial and transverse fibers may be selected in order to tailor the various fiber architectural designs to the specific performance requirements of the specific dental application in which they will be used. Typically, the thickness is selected so as to tailor the fiber orientations to an optimal direction and geometry required for a specific application. In embodiments, the ratio of the thickness of the axial yarns to the transverse fibers may be in the range from 1.1 to 1.0, to 6.0 to 1.0, but the thickness range may be greater than or less than those ranges. If desired, the axial and transverse fibers may also be formed of different chemical compositions. Generally, the axial yarns are all one thickness, and the transverse yarns are all a second, thinner thickness, but thicknesses in either of these groups could vary. However, given the small size of the dental appliances, varying the thickness would result in a ribbon that would likely be difficult to produce.

The fiber weave can be supplied preimpregnated with resins, or may be supplied in a dried state and impregnated with resins during application by a technician. The fiber fabric can be used with any variety of binders, and more preferably resins, used in the industry. Examples of fibers and resins that may be used are provided in Exhibit E, attached hereto, although applications herein are not limited to those fibers and resins.

FIGS. 1 and 2 represent cross-sections of a prior art weave material for use in forming a reinforced plastic for use as a dental appliance in accordance with the '951 patent and present embodiments, respectively. The axial direction for each of FIGS. 1 to 4 is from left to right in the figures, and the transverse direction is into and out of the page. In embodiments described herein, a fabric ribbon is formed, with the axial direction extended along the length of the ribbon, but the principals described herein may be utilized in other fabric structures for reinforced plastics.

As can be seen, the prior art ribbon 18 in FIG. 1 includes transverse fibers 24 and axial fibers 20, 22 having the same diameter, 2×. In contrast, the ribbon 26 of FIG. 2 includes axial yarns 28, 30 having a dimension of 2×, but transverse fibers 32 having a dimension of 1×. As discussed above, the difference in dimension can be selected according to an application, but for the purpose of this example in FIG. 2, the ratio of the thickness of the axial fibers 28, 30 to the transverse fibers 32 is greater than one to one, in this example, 2 to 1. In contrast, in the prior art ribbon of FIG. 1, the ratio of the thickness of the axial fibers 20, 22 to the transverse fibers 24 is 1 to 1.

Because the transverse fibers 32 in FIG. 2 are less thick than the transverse fibers 24 in FIG. 1, even though the spacing of adjacent transverse fibers 24, 32 in both FIGS. 1 and 2 is the same dimension y, the overall thickness (height in FIGS. 1 and 2) of each the ribbons 18, 26 is different. That is, the weaved ribbon 26 in FIG. 2 is less thick (5× in the example) from top to bottom in the figure than the prior art weaved ribbon 18 in FIG. 1 (6×, assuming all the fibers are of the thickness 2×).

By having the transverse fibers 32 thinner, the axial fibers 28, 30 in FIG. 2 do not have to turn as dramatically as the axial fibers 20,22 in FIG. 1, which must turn dramatically to curve their surfaces around the thicker transverse fibers 24. Thus, the thickness of the transverse fibers determines the directionality or the sinusoidal effect of the axial yarns.

Thus, the axial fibers 28, 30 are straighter over their length than the prior art axial fibers 20, 22. Fibers tend to perform differently in different directions. Fibers carry loads only in tension. Fiber characteristics are directionally dependent, and carry their greatest loads when they are straight. Fibers that are sinusoidal in nature, such as the axial fibers 20, 22 in FIGS. 1 and 4, are straightened before reaching their greatest load carrying capacity. The use of the thinner transverse fibers 32 in the ribbon 26 permits the transitions of the axial yarns 28, 30 to be on less steep slopes, more closely approximating linear alignment instead of sinusoidal. This arrangement allows for a stronger elastic performance characteristic in the direction of the axial yarns. The directionality of the yarns, or the sinusoidal effect, influences the slope of the stress-strain curve. By reducing the thickness of the transverse fibers 32, the axial fibers 30, 28 are more straight in an axial direction, and thus provide greater flexural strength in that direction. Thus, a stress-strain curve for the axial yarns is steeper than for a fiber ribbon having transverse fibers of a greater thickness. As is known, a reinforced plastic with straight axial fibers would provide an extremely steep curve (i.e., very little stretch would occur as a result of an axially applied load). In contrast, curvy or sinusoidal fibers would provide a more shallow curve, because those fibers could be stretched until straightened. This shallower curve represents elastic behavior of the fibers due to the ability to first stretch those fibers until they are straight. This elastic behavior is not typically present in straight fibers.

The use of the thinner transverse fibers 32 in the ribbon 26 permits the ribbon 26 to behave more like straight fibers than the prior art ribbon 18, and thus have the more steep stress-strain curve. This steeper curve represents stronger yield strength for the ribbon 26 over the prior art ribbon 18, which provides better performance for most dental applications.

Reduced thickness of the transverse fibers 32 provides other advantages. A ribbon, such as the ribbon 26, that includes thinner transverse fibers 32 results in less volume of resin at the bond line than a ribbon composed of thicker transverse fibers. The pockets formed between adjacent transverse fibers 32 at the outside of the weaved ribbon 26 are smaller than corresponding pockets on the prior art ribbon 18. This smaller pocket is represented in height by the dimension "a" for current embodiments shown in FIG. 3 and by the dimension "b" in the prior art embodiment shown in FIG. 4. Making these pockets smaller means that less resin is required to fill the pockets.

Use of less resin provides less opportunity for failures in the dental appliances formed utilizing the fiber structures of embodiments described herein. Non-ductile materials, such as dental resins and dental composite resins, fail due to defaults, voids and defects within them. The thin bond line provided by the ribbon 26 allows less resin to be used. Typical failures of the bond to the substrate in prior art ribbons, such as the ribbon 18, are initiated by the voids, defects, and faults in the resin. Therefore, the greater the volume of resin, the greater the probability for flaws, voids, or defects. Utilizing the ribbon 26 reduces the amount of resin needed for a bond.

Moreover, more surface area of the weaved ribbon 26 is in contact with a substrate 40 for the weaved ribbon 26 than the prior art weaved ribbon 18, which is spaced from the substrate 42 by the more extreme curvature of the axial fibers 20, 22. This arrangement permits the axial yarns 28, 30 have longer and closer tangential contact with the substrate 40. The thinner profile permits the axial yarns to more closely conform to the contours of the underlying substrate along the entire length of the axial yarns than a ribbon that is constructed with transverse fibers of a greater thickness. This feature allows less resin to be used, and ensures enhanced bonding of the dental appliance to the substrate.

Thus, there are two attachment advantages to the structure in FIG. 3 over the prior art structure in FIG. 4. First, for the ribbon 26 in FIG. 3, there is a smaller resin pocket in which failure can occur. Second, because the axial fibers 28, 30 are straighter, those fibers have a longer tangential contact with the substrate 40 for direct attachment to the substrate 40.

For the embodiment shown in FIGS. 2 and 3, even though the ribbon 26 has a lower profile and less resin for bonding to the substrate 40, the fiber thickness and fiber volume in the axial direction is the same as the thickness and volume in the axial direction of the prior art ribbon 18. Thus, even though the structure is smaller in volume and thickness, there is no corresponding loss in strength of the structure in the axial direction because the fibers in that direction are of the same thickness. In fact, as described above, because the axial fibers 28, 30 are straighter than the axial fibers 20, 22, the axial fibers 28, 30 provide greater flexural strength than the axial fibers 20, 22.

The ribbon 26 of FIG. 2 may be utilized in many different dental applications. The ribbon 26 is typically impregnated with a resin, or a resin may be added during application of the ribbon to a substrate.

For many dental applications of the ribbon 26, the dental ribbon 26 is attached to teeth. Therefore, the substrate 40 in embodiments herein is one or more teeth T (FIGS. 5 to 12). Resins are used to impregnate the fibers and attach the fibers of the ribbon 26 to the tooth substrate.

Figure 6:
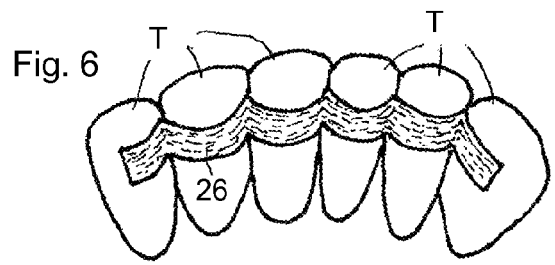

One common use for the ribbon 26 is for a periodontal splint, shown in FIGS. 5 and 6. In a periodontal splint, the ribbon 26 is aligned along adjacent teeth T to bond the teeth together. Examples of such a procedure are shown in Exhibits A, C and D, although those examples do not show use of the present embodiment of the dental ribbon 26. In contrast to prior art ribbons, such as the prior art ribbon 18 shown in FIG. 1, the ribbon 26, because of its low profile, can be adapted closer to the tooth substrate T, including deep into the interproximal contacts 52 between the teeth. This feature permits more of the tooth surface T to be bonded to the fiber ribbon 26, permitting less resin to be used at this bond line, and providing a better attachment of the ribbon 26 to the tooth substrate. As such, such bonding aids in preventing debonding of the extracoronal wing.

Figure 7:
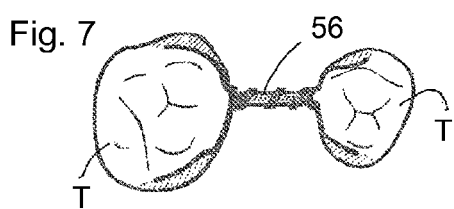
FIGS. 7 and 8 are representations of applications of the fabric ribbon of FIG. 2 to form pontic beams.
Figure 8:
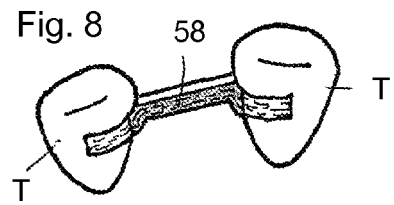

Another application for the ribbon 26 is in a pontic beam 56 or 58, such as is shown in FIGS. 7 and 8. Instructions for pontic beam installation are shown at Exhibit B, but again not with the present ribbon 26. For the pontic beams 56, 58, the greater elastic rigidity of the ribbon 26 minimizes deformation of the ribbon, providing more rigidity for the beams.

Figure 9:
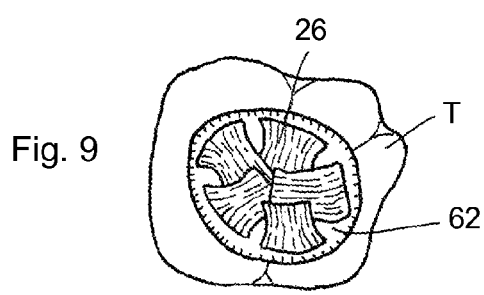
FIGS. 9-11 is a representations of applications of the fabric ribbon of FIG. 2 to form composite restorations.
Figure 10:
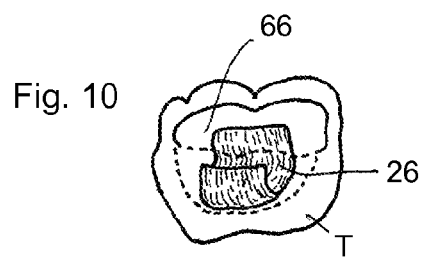
Figure 11:
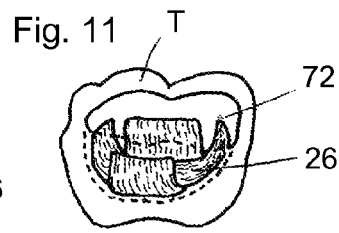

Still another application for the ribbon 26 is for composite restorations. Examples are shown in FIGS. 9, 10, and 11. In composite restorations, the ribbon material 26 is impregnated with a resin to form a reinforced plastic that may be used to fill a cavity in a tooth T. As examples, different cavities 62, 66, and 72 are lined with the ribbon 26 and a resin is added to form a composite restoration. As described above, the low profile of the ribbon 26 permits the ribbon to contour to a surface with much more of the fiber contacting the surface than in prior art reinforced plastic composite restorations. Because the ribbon 26 may be more closely adapted to the inside surface of the cavity that the ribbon is filling, there is a greater fiber effect and less resin effect within the composite restoration. Because the fibers are more closely adapted to and provide more surface to contact to the teeth, the effects of polymer shrinkage of the resin are decreased in the composite restorative material. As such, the strains that are induced within the remaining tooth structure are decreased. Lessening the polymer shrinkage also diminishes leakage between the restoration and the tooth. Diminishing the leakage diminishes tooth sensitivity and the reoccurrence of decay.

Figure 12:
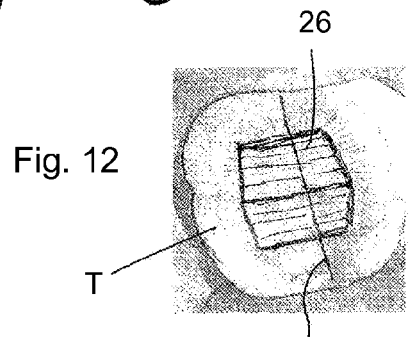
FIG. 12 is a representation of application of the fabric ribbon of FIG. 2 to form a bridge across a crack in a tooth.

Another application is shown in FIG. 12, where a crack 80 is developing at the base of a cavity. The ribbon 26 may be used to bridge the crack. Because the ribbon 26 is more closely adaptable to the tooth substrate and the axial fibers are stiffer and the direction of these fibers can be aligned to extend across the crack, the crack may be more effectively bridged. The thin bond line described above and the rigidity of the ribbon 26 minimize shear and effects of the "Poison Effect."

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A dental appliance, comprising:
   a fabric ribbon configured for dental purposes and for use in a reinforced plastic composite, comprising:
   a transverse set of fibers aligned generally transverse to a length of the ribbon, wherein the length of the ribbon corresponds to a dimension of the ribbon in a direction along which the ribbon carries a greatest tensile load; and
   an axial set of fibers, intertwined around the transverse set of fibers and aligned generally axially along the length of the ribbon, each of the fibers in the axial set of fibers having a thickness greater than a thickness of each of the fibers in the transverse set of fibers;
   wherein the transverse set of fibers comprises at least a first transverse fiber and a second transverse fiber that are adjacent to one another along the length of the ribbon, wherein the axial set of fibers is intertwined around the transverse set of fibers such that the first transverse fiber and the second transverse fiber are separated from one another by at least one fiber from the axial set of fibers and such that a first thickness of the ribbon at the first transverse fiber is equal to a second thickness of the ribbon at the second transverse fiber.

2. The dental appliance of claim 1, further comprising a resin matrix applied to the fabric ribbon.

3. The dental appliance of claim 1, wherein the ribbon is a leno weave fabric.

4. The dental appliance of claim 3, wherein the transverse set of fibers comprises filler or weft fibers for the leno weave fabric and the axial set of fibers comprises warp fibers for the leno weave fabric.

5. The dental appliance of claim 3, wherein a ratio of the diameter of the fibers in the axial set of fibers to the diameter of the fibers in the transverse set of fibers is at least 1.1 to 1.

6. The dental appliance of claim 3, wherein a ratio of the diameter of the fibers in the axial set of fibers to the diameter of the fibers in the transverse set of fibers is at least greater than or equal to 2 to 1.

7. The dental appliance of claim 3, wherein a ratio of the diameter of the fibers in the axial set of fibers to the diameter of the fibers in the transverse set of fibers is at least greater than or equal to 6 to 1.

8. The dental appliance of claim 1, wherein each of the fibers in the axial set of fibers has a first thickness greater than a second thickness of each of the fibers in the transverse set of fibers so that each of the fibers in the axial set of fibers is straighter and exhibits a stronger elastic performance characteristic in comparison to an arrangement in which the thickness of each of the fibers in the transverse set of fibers is greater than the second thickness.

9. The dental appliance of claim 8, wherein the fabric ribbon is configured to conform against a substrate along the length of the ribbon, and wherein each of the fibers in the axial set of fibers has the first thickness greater than the second thickness of each of the fibers in the transverse set of fibers so that an outside of the fibers in the axial set of fibers has a larger amount of surface area for contacting the substrate when conforming against the substrate in comparison to an arrangement in which the thickness of each of the fibers in the transverse set of fibers is greater than the second thickness.

10. The dental appliance of claim 9, further comprising a resin matrix applied to the fabric ribbon for attaching the fabric ribbon to the substrate, wherein each of the fibers in the axial set of fibers has the first thickness greater than the second thickness of each of the fibers in the transverse set of fibers so that an outside of the fibers in the axial set of fibers forms a smaller volume for receiving the resin matrix between the outside of the axial fibers and the substrate during attachment to the substrate in comparison to an arrangement in which the thickness of each of the fibers in the transverse set of fibers is greater than the second thickness.

11. The dental appliance of claim 1, wherein the ribbon is a plain weave fabric.

12. The dental appliance of claim 1, wherein the ribbon is a triaxial braided fabric.

* * * * *